US006825179B2

United States Patent
Nielsen et al.

(10) Patent No.: US 6,825,179 B2
(45) Date of Patent: Nov. 30, 2004

(54) ACTIVE INGREDIENT COMBINATIONS OR ADDUCTS OF CYCLODEXTRINS AND QUINONES

(75) Inventors: Jens Nielsen, Henstedt-Ulburg (DE); Heiner Max, Hamburg (DE); Birgit Hargens, Hamburg (DE); Ralph Schimpf, Hamburg (DE)

(73) Assignee: Beiersdorf AG, Hamburg (DE)

( * ) Notice: Subject to any disclaimer, the term of this patent is extended or adjusted under 35 U.S.C. 154(b) by 236 days.

(21) Appl. No.: 09/907,171

(22) Filed: Jul. 17, 2001

(65) Prior Publication Data

US 2002/0045596 A1 Apr. 18, 2002

(30) Foreign Application Priority Data

Jul. 21, 2000 (DE) .......................................... 100 35 513

(51) Int. Cl.[7] ...................... A01N 43/04; A61K 31/715
(52) U.S. Cl. ........................ 514/58; 514/54; 536/102; 536/103; 536/103.1
(58) Field of Search ................................ 536/102, 103, 536/103.1; 514/54, 58

(56) References Cited

U.S. PATENT DOCUMENTS

| 4,511,564 A | * | 4/1985 | Ishizuka et al. ............ 514/167 |
| 5,631,244 A | | 5/1997 | Galons et al. |
| 5,989,583 A | * | 11/1999 | Amselem .................... 424/439 |

FOREIGN PATENT DOCUMENTS

| DE | 195 37 027 A1 | 4/1997 |
| DE | 694 04 546 T2 | 3/1998 |
| EP | 0 233 615 A2 | 8/1987 |
| EP | 0 624 599 B1 | 11/1994 |
| EP | 0 624 599 A2 | 11/1994 |
| FR | 2 640 136 A1 | 6/1990 |
| JP | 56109590 A | 8/1981 |
| WO | WO 91/18589 | 12/1991 |

OTHER PUBLICATIONS

XP 002260641 Database WPI, Section Ch, Week 198141, Derwent Publication Ltd., London, GB; AN 1981–74927D & JP 56 109590 A (Zeria Shinyaku Kogyo KK), Aug. 31, 1981.

XP 002260642 Database WPI, Section Ch, Week 198417, Derwent Publications Ltd., London, GB; AN 1984–104277 & JP 59 047202 A (Zeria Shinyaku Kogyo KK), März 16,1984 (Mar. 16, 1984).

XP 002260643 Database WPI, Section Ch, Week 098403 DErwent Publications Ltd., London, GB; AN 1984–014258 & JP 206540 A (Fujisawa Pharm Co Ltd), Dezember 1, 1983 (Dec. 1, 1983).

XP 002260644 Database WPI Section Ch, Week 198821 Derwent Oublications Ltd., London, GB; AN 1998–142663 & JP 63 083021 A (KAO Corp), Apr. 13, 1988.

* cited by examiner

*Primary Examiner*—Samuel Barts
*Assistant Examiner*—Patrick Lewis
(74) *Attorney, Agent, or Firm*—Norris McLaughlin & Marcus PA

(57) ABSTRACT

Active ingredient combinations of cyclodextrins and at least one quinone and/or at least one hydroquinone for use in cosmetic or dermatological formulations.

17 Claims, No Drawings

ACTIVE INGREDIENT COMBINATIONS OR ADDUCTS OF CYCLODEXTRINS AND QUINONES

The present invention relates to cosmetic or dermatological preparations comprising active ingredients for the care and protection of the skin, in particular sensitive skin and dry skin and, very particularly, skin ageing or aged by intrinsic and/or extrinsic factors, and for assisting the skin's own lipid metabolism, and to the use of such active ingredients and combinations of such active ingredients in the field of cosmetic and dermatological skincare.

The term "cosmetic skincare" primarily means the strengthening or rebuilding of the skin's natural function as a barrier against environmental influences (e.g. dirt, chemicals, microorganisms) and against the loss of endogenous substances (e.g. water, natural fats, electrolytes).

Impairment of this function may lead to increased resorption of toxic or allergenic substances or attack by microorganisms, leading to toxic or allergic skin reactions.

Another aim of skincare is to compensate for the loss by the skin of lipids and water caused by daily washing. This is particularly important when the natural regeneration ability is insufficient. Furthermore, skincare products should protect against environmental influences, in particular against sun and wind, and delay skin ageing.

Chronological skin ageing is caused, for example, by endogenous genetically determined factors. The following structural damage and functional disorders, which can also fall under the term "senile xerosis", result, for example, in the epidermis and dermis as a result of ageing:

a) dryness, roughness and formation of dryness wrinkles,
b) itching and
c) reduced refatting by sebacious glands (e.g. after washing).

Exogenous factors, such as UV light and chemical noxae, can have a cumulative effect and, for example, accelerate or supplement the endogenous ageing processes. In the epidermis and dermis, for example, the following structural damage and functional disorders appear in the skin as a result of exogenous factors; these go beyond the extent and quality of the damage in the case of chronological ageing:

d) visible vascular dilation (telangiectases, couperosis);
e) flaccidity and formation of wrinkles;
f) local hyperpigmentation, hypopigmentation and abnormal pigmentation (e.g. age spots) and
g) increased susceptibility to mechanical stress (e.g. cracking).

The present invention relates in particular to products for the care of skin aged naturally, and to the treatment of the damage caused by photoageing, in particular of the phenomena listed under a) to g).

Products for the care of aged skin are known per se. They comprise, for example, retinoids (vitamin A acid and/or derivatives thereof) or vitamin A and/or derivatives thereof. The degree of their effect on structural damage is, however, limited. Furthermore, in product development there are considerable difficulties in stabilizing the active ingredients to an adequate extent against oxidative decay. The use of products comprising vitamin A acid, moreover, often causes severe erythematous skin irritations. Retinoids can therefore only be used in low concentration.

In particular, the present invention relates to cosmetic preparations having effective protection against harmful oxidation processes in the skin, but also for the protection of cosmetic preparations themselves or for the protection of the constituents of cosmetic preparations against harmful oxidation processes.

The present invention further relates to antioxidants, preferably those used in skincare cosmetic or dermatological preparations. In particular, the invention also relates to cosmetic and dermatological preparations comprising such antioxidants. In a preferred embodiment, the present invention relates to cosmetic and dermatological preparations for the prophylaxis and treatment of cosmetic and dermatological skin changes, such as, for example, skin ageing, in particular skin ageing caused by oxidative processes.

Furthermore, the present invention relates to active ingredients and preparations comprising such active ingredients for the cosmetic and dermatological treatment or prophylaxis of erythematous, inflammatory, allergic or autoimmune-reactive symptoms, in particular dermatoses.

In a further advantageous embodiment, the present invention relates to active ingredient combinations and preparations which serve for the prophylaxis and treatment of light-sensitive skin, in particular of photodermatoses.

The harmful effect of the ultraviolet part of solar radiation on the skin is generally known. Whereas rays with a wavelength of less than 290 nm (the UVC region) are absorbed by the ozone layer in the earth's atmosphere, rays in the range between 290 nm and 320 nm, the UVB region, cause erythema, simple sunburn or even burns of greater or lesser severity.

A maximum erythema activity of sunlight is given as the relatively narrow range around 308 nm.

Numerous compounds are known for protecting against UVB radiation; these are derivatives of 3-benzylidenecamphor, 4-aminobenzoic acid, cinnamic acid, salicylic acid, benzophenone and also 2-phenylbenzimidazole.

It is also important to have available filter substances for the range between about 320 nm and about 400 nm, the UVA region, since its rays can cause reactions in cases of photosensitive skin. It has been found that UVA radiation leads to damage of the elastic and collagenous fibres of connective tissue, which leads to premature ageing of the skin, and is to be regarded as a cause of numerous phototoxic and photoallergic reactions. The harmful effect of UVB radiation can be intensified by UVA radiation.

To protect against rays of the UVA region, certain derivatives of dibenzoylmethane are therefore used, the photostability of which is inadequate (Int. J. Cosm. Science 10, 53 (1988)).

The UV radiation can, however, also lead to photochemical reactions, in which case the photochemical reaction products then intervene in the skin metabolism.

Such photochemical reaction products are predominantly free-radical compounds, for example hydroxyl radicals. Undefined free-radical photoproducts which form in the skin itself can also display uncontrolled secondary reactions because of their high reactivity. However, singlet oxygen, a non-free-radical excited state of the oxygen molecule, can also be formed during UV irradiation, as can short-lived epoxides and many others. Singlet oxygen, for example, differs from normal triplet oxygen (free-radical ground state) by virtue of its increased reactivity. However, excited, reactive (free-radical) triplet states of the oxygen molecule also exist.

UV radiation is also a type of ionizing radiation. There is therefore the risk that ionic species will also form during UV exposure, which then for their part are able to intervene oxidatively in the biochemical processes.

In order to prevent these reactions, additional antioxidants and/or free-radical scavengers can be incorporated into the cosmetic or dermatological formulations.

It has already been proposed to use vitamin E, a substance with known antioxidative action, in sunscreen formulations, although, here too, the effect achieved falls a long way short of expectations.

The object of the invention was therefore to provide cosmetic, dermatological and pharmaceutical active ingredients and preparations, and sunscreen formulations which serve for the prophylaxis and treatment of photosensitive skin, in particular photodermatoses, preferably PLD.

Other names for polymorphous photodermatosis are PLD, PLE, Mallorca acne and a large number of other names, as given in the literature (e.g. A. Voelckel et al, Zentralblatt Hautund Geschlechtskrankheiten (1989), 156, p.2).

Erythematous skin symptoms also occur as accompanying symptoms in certain skin diseases or irregularities. For example, the typical skin rash symptom of acne is generally red to a greater or lesser extent.

Antioxidants are mainly used as substances which protect against the deterioration of the preparations in which they are present. Nevertheless, it is known that in human or animal skin as well undesired oxidation processes may occur. Such processes play an important role in skin ageing.

The essay "Skin Diseases Associated with Oxidative Injury" in "Oxidative Stress in Dermatology", p. 323 ff. (Marcel Decker Inc., New York, Basel, Hong Kong, Editor: Jürgen Fuchs, Frankfurt, and Lester Packer, Berkeley/Calif.) discusses oxidative skin damage and its more obvious causes.

Also for the reason of preventing such reactions, antioxidants and/or free-radical scavengers can be additionally incorporated into cosmetic or dermatological formulations.

A number of antioxidants and free-radical scavengers are known. For example U.S. Pat. Nos. 4,144,325 and 4,248,861, and numerous other documents have already proposed the use of vitamin E, a substance with known antioxidative action in sunscreen formulations, although here too the effect achieved falls a long way short of the desired effect.

The object of the present invention was therefore to find ways of avoiding the disadvantages of the prior art. In particular, the effect of repairing damage associated with endogenous, chronological and exogenous skin ageing and the prophylaxis should be permanent, sustained and without the risk of side effects.

To overcome these shortcomings was the object of the present invention.

Also known, from DE-A-33 09 850, are cosmetic formulations containing Coenzyme Q-10, which are suitable for the treatment of skin diseases, for the prophylaxis of dystrophic and dysmetabolic conditions of the skin and for use in cases of chemical and physical respiratory damage or in cases of delayed respiration associated with age and wear.

Coenzyme Q-10 is characterized by the following structural formula

10

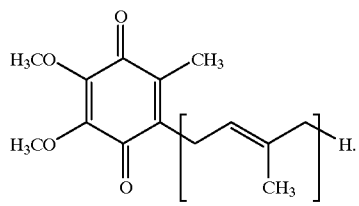

Japanese laid-open specification 58,180,410 describes the suitability of Coenzyme Q-10 for cosmetics. It is said to activate skin cell metabolism and to suppress oxidation. As a result, Coenzyme Q10 has an important function in the prevention of skin damage caused by UV rays and in the prevention skin ageing. In 20- to 40-year olds, the roughness of the skin is improved by giving the skin moisture.

It was therefore surprising and could not have been foreseen by the person skilled in the art that active ingredient combinations of cyclodextrins and at least one quinone and/or at least one hydroquinone overcome the disadvantages of the prior art.

According to the invention, the quinones may be advantageously be chosen from the group of bioquinones. Bioquinones are prenylated quinones which occur in the animal and plant kingdom, where they perform biochemical functions. Particular preference is given to ubiquinones and plastoquinones.

According to the invention, the hydroquinones may advantageously be chosen from the group of reduced forms of the corresponding bioquinones, i.e. particularly preferably ubiquinols and plastoquinols.

Ubiquinones are the most widespread and therefore the most investigated bioquinones. Ubiquinones are referred to as Q-1, Q-2, Q-3 etc. depending on the number of isoprene units linked in the side chain, or as U-5, U-10, U-15 etc. according to the number of carbon atoms. They arise preferentially with certain chain lengths, e.g. in some microorganisms and yeasts where n=6. In the case of most mammals, including man, Q-10 predominates.

Ubiquinones serve the organisms as electron carriers in the respiration chain. They are located in the mitochondria where they permit cyclic oxidation and reduction of the substrates of the citric acid cycle.

Plastoquinones have the general structural formula

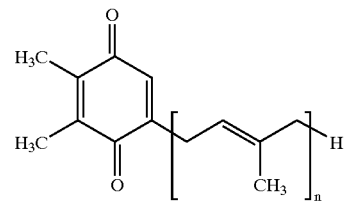

They can be isolated from chloroplasts and play a role as redox substrates in photosynthesis in the case of cyclic and noncyclic electron transportation, being reversibly converted to the corresponding hydroquinones (plastoquinol). Plastoquinones differ in the number n of isoprene radicals and are named accordingly, e.g. PQ-9 (n=9). Other plastoquinones with varying substituents on the quinone ring also exist.

Cyclodextrins (cycloamyloses, cycloglucans) are known per se in cosmetic and pharmaceutical preparations. These substances are often used for "molecular encapsulation", i.e. as a protective coating of sensitive molecules. These are 6, 7, 8 or even more α-1,4-linked glucose units, cyclohexaamylose (α-cyclodextrin) being characterized by the structure

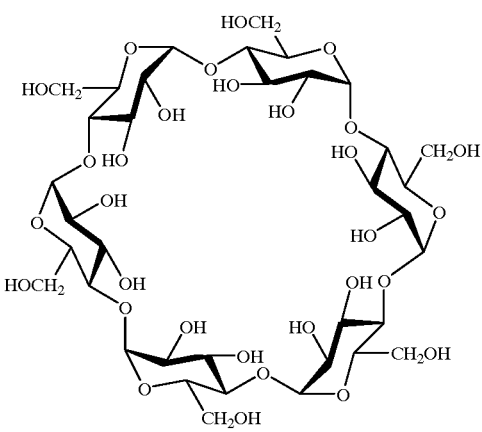

Cycloheptaamylose (β-cyclodextrin) is characterized by the structure

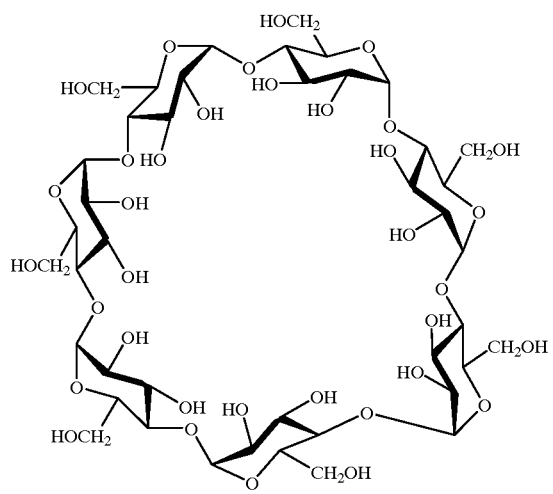

Cyclooctaamylose (γ-cyclodextrin) is characterized by the structure

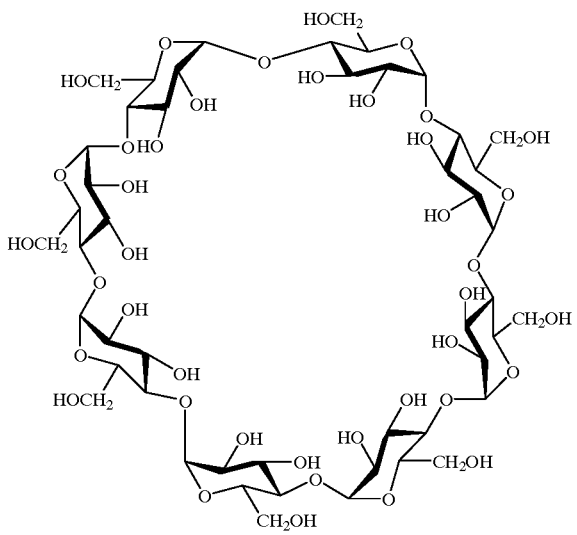

Cycloenneaamylose (8-cyclodextrin) is characterized by the structure

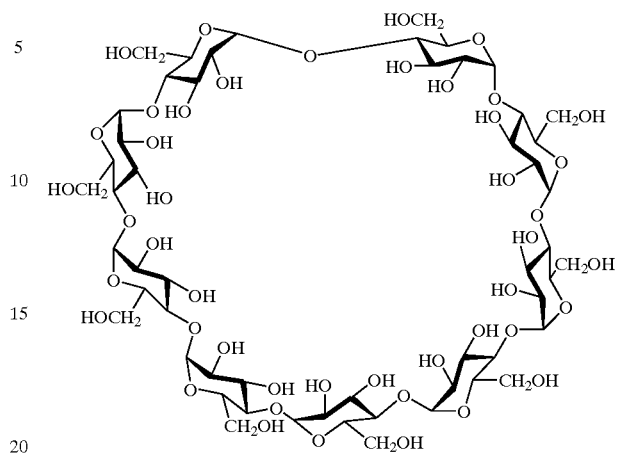

Within the scope of this patent, polar- and nonpolar-substituted cyclodextrins can also be used. These preferably include, but not exclusively, methyl-, ethyl- and hydroxypropyl-cyclodextrin.

The active ingredient combinations according to the invention can be incorporated without problems into customary cosmetic preparations, advantageously sunscreen preparations, but also, if desired, other preparations, for example pharmaceutical preparations.

The use of the active ingredient used according to the invention or of cosmetic or topical dermatological preparations with an effective content of active ingredient used according to the invention surprisingly enables effective treatment, but also prophylaxis

- of deficient, sensitive or hypoactive skin states or deficient, sensitive or hypoactive states of skin appendages,
- of signs of premature ageing of the skin (e.g. wrinkles, age spots, teleangiectases) and/or of the skin appendages,
- of environmentally induced changes in the skin and the skin appendages (smoking, smog, reactive oxygen species, free radicals) and in particular light-induced negative changes,
- of dry skin,
- of light-induced skin damage,
- of pigmentation disorders,
- of irritation,
- of dry skin conditions and impairment of the horny layer barrier,
- of hair loss and for improved hair growth,
- of inflammatory skin conditions, such as atopic eczema, seborrhoeic eczema, polymorphous photodermatosis, psoriasis, vitiligo.

The active ingredient according to the invention or cosmetic or dermatological preparations with an effective content of active ingredient according to the invention, however, also surprisingly serves

- to calm sensitive or irritated skin
- to stimulate the synthesis of collagen, hyaluronic acid and elastin,
- to stimulate intracellular DNA synthesis, in particular in cases of deficient or hypoactive skin states,
- to increase cell renewal and regeneration of the skin, to increase the skin's own protective and repair mechanisms (for example for dysfunctional enzymes, DNA, lipids, proteins), for the pre- and post-treatment in cases of topical application of laser and abrasive treatments, which serve, for example, to reduce skin wrinkles and scars, to counteract the resulting skin irritations and to promote the regeneration processes in the damaged skin.

Neither had it been foreseen that the quinones or hydroquinones in the active ingredient combinations according to the invention have greater stability toward a physical or chemical effect, in particular the effect of UV light, than if they have not been combined with cyclodextrins.

In particular, according to the invention, it is extremely advantageous to use the active ingredient used according to the invention or cosmetic or topical dermatological preparations with an effective content of active ingredient used according to the invention for the cosmetic or dermatological treatment or prophylaxis of undesired skin conditions.

It is assumed that at least in the case of the previously described direct combination of the substances, molecular adducts according to the invention of cyclodextrins and at least one quinone and/or at least one hydroquinone are obtained. Thus, in the text below, molecular adducts according to the invention are also intended where active ingredient combinations according to the invention of cyclodextrins and at least one quinone and/or at least one hydroquinone are discussed.

There are good reasons for assuming that such molecular adducts, by analogy with other molecular adducts of cyclodextrins, follow the scheme below:

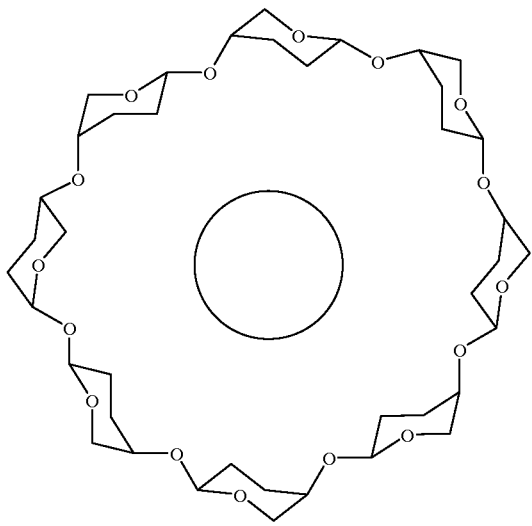

In this scheme, which is to be accepted as probable, the cyclodextrin backbones represent the host molecule, and the quinone or hydroquinone in question, which are shown here by the circle inside the scheme, represent the guest molecule.

Because of the calculated molar ratios, active ingredient combinations according to the invention are also possible which are to be regarded with some probability as molecular adducts in which two, optionally even more, identical or different guest molecules, which are shown here by circles inside the scheme, are present in encapsulated form in one host molecule as if on a molecular plane. This is indicated in the scheme below.

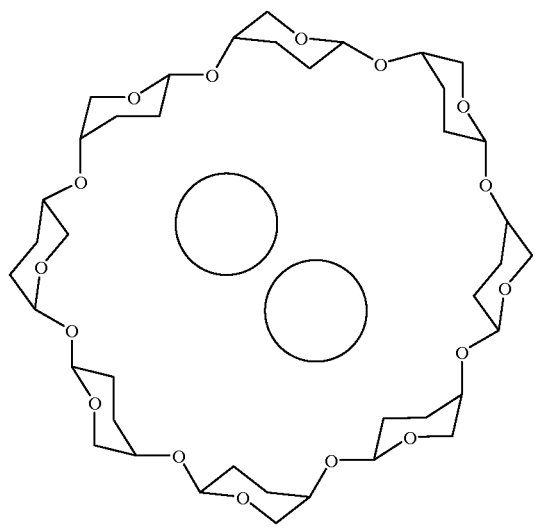

Such molecular adducts are preferably formed by directly combining the individual parent substances, particularly preferably if the combination is carried out in the presence of a suitable solvent.

Molecular adducts according to the invention of cyclodextrins and active ingredient combinations of cyclodextrins and at least one quinone and/or at least one hydroquinone can advantageously be obtained, for example, by dissolving cyclodextrins in water and adding the at least one quinone and/or at least one hydroquinone. The respective molecular adduct thereupon precipitates out as a solid and can be subjected to customary purification and work-up steps.

The total amount of at least one quinone and/or at least one hydroquinone in the finished cosmetic or dermatological preparations is advantageously chosen from the range 0.001–10.0% by weight, preferably 0.01–5.0% by weight, based on the total weight of the preparations.

The total amount of cyclodextrins, in particular β-cyclodextrin and/or γ-cyclodextrin in the finished cosmetic or dermatological preparations is advantageously chosen from the range 0.001–20.0% by weight, preferably 0.02–10.0% by weight, based on the total weight of the preparations.

It is particularly advantageous to choose weight ratios of cyclodextrins to at least one quinone and/or at least one hydroquinone as 10:1 to 1:5, preferably as 8:1 to 1:2, particularly preferably as 4:1 to 1:1.

Active ingredient combinations which are regarded as particularly advantageous molecular adducts of cyclodextrins and at least one quinone and/or at least one hydroquinone are those which have the following molar ratios:

1 mol of α-cyclodextrin:1 mol of quinone and/or hydroquinone
1 mol of β-cyclodextrin:1 mol of quinone and/or hydroquinone
1 mol of γ-cyclodextrin:1 mol of quinone and/or hydroquinone
2 mol of α-cyclodextrin:1 mol of quinone and/or hydroquinone
2 mol of β-cyclodextrin:1 mol of quinone and/or hydroquinone
2 mol of γ-cyclodextrin:1 mol of quinone and/or hydroquinone
1 mol of α-cyclodextrin:2 mol of quinone and/or hydroquinone 1 mol of β-cyclodextrin:2 mol of quinone and/or hydroquinone 1 mol of γ-cyclodextrin:2 mol of quinone and/or hydroquinone 3 mol of α-cyclodextrin:1 mol of quinone and/or hydroquinone 3 mol of β-cyclodextrin:1 mol of quinone and/or hydroquinone 3 mol of γ-cyclodextrin:1 mol of quinone and/or hydroquinone Active ingredient combinations preferred according to the invention relate to Coenzyme Q10 and γ-cyclodextrin, particularly preferably in molar ratios of γ-cyclodextrin to Coenzyme Q10 as 1.5:1 to 2.5:1, in particular about 2:1.

Although not absolutely necessary, cosmetic and dermatological preparations according to the invention also advantageously comprise inorganic pigments based on metal oxides and/or other metal compounds which are insoluble or sparingly soluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals and mixtures of such oxides. Particular preference is given to pigments based on $TiO_2$.

According to the invention, the inorganic pigments are advantageously in hydrophobic form, i.e. have been surface-treated to repel water. This surface treatment may involve providing the pigments with a thin hydrophobic layer by methods known per se.

Such a process comprises, for example, producing the hydrophobic surface layer by a reaction according to

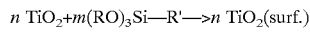

$n$ $TiO_2 + m(RO)_3Si\text{—}R' \rightarrow n\ TiO_2(\text{surf.})$ n and m are stoichiometric parameters to be used as desired, and R and R' are the desired organic radicals. Hydrophobicized pigments prepared, for example, analogously to DE-A 33 14 742 are advantageous.

Advantageous $TiO_2$ pigments are obtainable, for example, under the trade names T 805 from Degussa.

The total amount of inorganic pigments, in particular hydrophobic inorganic micropigments in the finished cosmetic or dermatological preparations is advantageously chosen from the range 0.1–30% by weight, preferably 0.1–10.0% by weight, in particular 0.5–6.0% by weight, based on the total weight of the preparations.

The cosmetic and/or dermatological light protection formulations according to the invention can have the customary composition and can be used for cosmetic and/or dermatological light protection, and also for the treatment, care and cleansing of the skin and/or hair and as a make-up product in decorative cosmetics.

For use, the cosmetic and dermatological preparations according to the invention are applied to the skin and/or hair in an adequate amount in the manner customary for cosmetics.

Particularly preferred cosmetic and dermatological preparations are those which are present in the form of a sunscreen. These can advantageously additionally comprise at least one further UVA filter and/or at least one further UVB filter and/or at least one inorganic pigment, preferably an inorganic micropigment.

The cosmetic and dermatological preparations according to the invention can comprise cosmetic auxiliaries such as are usually used in such preparations, for example preservatives, bactericides, perfumes, antifoams, dyes, pigments which have a colouring action, thickeners, moisturizers and/or humectants, fats, oils, waxes or other customary constituents of a cosmetic or dermatological formulation, such as alcohols, polyols, polymers, foam stabilizers, electrolytes, organic solvents or silicone derivatives.

An additional content of antioxidants is generally preferred. According to the invention favourable antioxidants which can be used are all the antioxidants which are suitable or customary for cosmetic and/or dermatological uses.

The antioxidants are advantageously chosen from the group consisting of amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine buthionine sulphones, penta-, hexa- and heptathionine-sulphoximine) in very low tolerated doses (for example pmol to μmol/kg), and furthermore (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, vitamin C and derivatives (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example selenium methionine), stilbenes and derivatives thereof (for example stilbene oxide, trans-stilbene oxide) and the derivatives of these active ingredients mentioned which are suitable according to the invention (salts, esters, ethers, sugars, nucleotides, nucleosides, peptides and lipids).

The amount of the abovementioned antioxidants (one or more compounds) in the preparations is preferably from 0.001 to 30% by weight, particularly preferably 0.05–20% by weight, in particular 0.1–10% by weight, based on the total weight of the preparation.

The prophylaxis or the cosmetic or dermatological treatment with the active ingredient used according to the invention or with the cosmetic or topical dermatological preparations having an effective content of active ingredient used according to the invention is carried out in the usual manner, mainly by applying the active ingredient used according to the invention or the cosmetic or topical dermatological preparations having an effective content of active ingredient used according to the invention to the affected areas of skin.

The active ingredient used according to the invention can advantageously be incorporated into customary cosmetic and dermatological preparations which may be in a variety of forms. They can, for example, be a solution, an emulsion of the water-in-oil (W/O) type or of the oil-in-water (O/W) type, or a multiple emulsion, for example of the water-in-oil-in-water (W/O/W) type or oil-in-water-in-oil (O/W/O) type, a hydrodispersion or lipodispersion, a gel, a solid stick or as an aerosol.

Emulsions according to the invention for the purposes of the present invention, e.g. in the form of a cream, a lotion, a cosmetic milk, are advantageous and comprise, for example, fats, oils, waxes and/or other fatty substances, and water and one or more emulsifiers as are customarily used for this type of formulation.

It is also possible and advantageous for the purposes of the present invention to incorporate the active ingredient used according to the invention into aqueous systems or surfactant preparations for cleansing the skin and the hair.

The person skilled in the art is of course aware that demanding cosmetic compositions are mostly inconceivable without customary auxiliaries and additives. Examples thereof include bodying agents, fillers, perfume, dyes, emulsifiers, additional active ingredients, such as vitamins or proteins, light protection agents, stabilizers, insect repellents, alcohol, water, salts, and antimicrobially, proteolytically or keratolytically active substances etc.

Corresponding requirements apply mutatis mutandis to the formulation of medicinal preparations.

Medicinal topical compositions for the purposes of the present invention generally comprise one or more medicaments in an effective concentration. For the sake of simplicity, for a clear distinction between cosmetic and medicinal application and corresponding products, reference is made to the legal provisions of the Federal Republic of Germany (e.g. Cosmetics Directive, Foods and Drugs Act).

In this connection, it is likewise advantageous to add the active ingredient used according to the invention as an additive to preparations which already comprise other active ingredients for other purposes.

Accordingly, for the purposes of the present invention, cosmetic or topical dermatological compositions can, depending on their formulation, be used, for example, as skin protection cream, cleansing milk, sunscreen lotion, nourishing cream, day or night cream, etc. In some instances it is possible and advantageous to use the compositions according to the invention as bases for pharmaceutical formulations.

Also favourable in some instances are cosmetic and dermatological preparations which are in the form of a sunscreen. As well as the active ingredient used according to the invention, these preferably additionally comprise at least one UVA filter substance and/or at least one UVB filter substance and/or at least one inorganic pigment.

It is, however, also advantageous for the purposes of the present invention to provide cosmetic and dermatological preparations whose main purpose is not protection against sunlight, but which nevertheless have a content of UV protection substances. Thus, for example, UV-A and/or UV-B filter substances are usually incorporated into day creams.

Preparations according to the invention can advantageously comprise substances which absorb UV radiation in the UVB region, the total amount of filter substances being, for example, 0.1% by weight to 30% by weight, preferably 0.5 to 10% by weight, in particular 1 to 6% by weight, based on the total weight of the preparations.

The UVB filters can be oil-soluble or water-soluble. Examples of oil-soluble substances are:

3-benzylidenecamphor and derivatives thereof, e.g. 3-(4-methylbenzylidene)camphor, 4-aminobenzoic acid derivatives, preferably 2-ethylhexyl 4-(dimethylamino)benzoate, amyl 4-(dimethylamino) benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl) 4-methoxybenzalmalonate;

2,4,6-trianilino(p-carbo-2'-ethyl-1'-hexyloxy)-1,3,5-triazine.

Advantageous water-soluble substances are:

2-phenylbenzimidazole-5-sulphonic acid and salts thereof, e.g. sodium, potassium or tri-ethanolammonium salts;

sulphonic acid derivatives of benzophenones, preferably 2-hydroxy-4-methoxybenzo-phenone-5-sulphonic acid and its salts;

sulphonic acid derivatives of 3-benzylidenecamphor, such as, for example, 4-(2-oxo-3-bornylidenemethyl) benzene-sulphonic acid, 2-methyl-5-(2-oxo-3-bornylidenemethyl)-sulphonic acid and its salts.

The list of said UVB filters which can be used according to the invention is of course not intended to be limiting.

The invention also provides the combination of a UVA filter according to the invention with a UVB filter or a cosmetic or dermatological preparation according to the invention which also comprises a UVB filter.

It can also be advantageous to use UVA filters which are customarily present in cosmetic and/or dermatological preparations in preparations according to the invention. Such filter substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)-propane-1,3-dione. Preparations which comprise these combinations are also provided by the invention. It is possible to use the same amounts of UVA filter substances which have been given for UVB filter substances.

Cosmetic and/or dermatological preparations for the purposes of the present invention can also comprise inorganic pigments which are customarily used in cosmetics for protecting the skin against UV rays. These are oxides of titanium, zinc, iron, zirconium, silicon, manganese, aluminium, cerium and mixtures thereof, and modifications in which the oxides are the active agents. Particular preference is given to pigments based on titanium dioxide. It is possible to use the amounts given for the above combinations.

The cosmetic and dermatological preparations according to the invention can comprise cosmetic active ingredients, auxiliaries and/or additives as are customarily used in such preparations, e.g. antioxidizing agents, preservatives, bactericides, perfumes, antifoams, dyes, pigments which have a colouring action, thickeners, surface-active substances, emulsifiers, emollients, moisturizers and/or humectants, fats, oils, waxes or other customary constituents of a cosmetic or dermatological formulation, such as alcohols, polyols, polymers, foam stabilizers, electrolytes, organic solvents or silicone derivatives.

If the cosmetic or dermatological preparation for the purposes of the present invention is a solution or emulsion or dispersion, solvents which may be used are:

water or aqueous solutions;
oils, such as triglycerides of capric or caprylic acid, but preferably castor oil;
fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;
alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the abovementioned solvents are used. In the case of alcoholic solvents, water can be a further constituent.

The oil phase of the emulsions, oleogels or hydrodispersions or lipodispersions for the purposes of the present invention is advantageously chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldec erucyl oleate, erucyl erucate, and synthetic, semisynthetic and natural mixtures of such esters, e.g. jojoba oil.

The oil phase can also advantageously be chosen from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from 8 to 24 carbon atoms, in particular 12–18 carbon atoms. The fatty acid triglycerides can,for example, be advantageously chosen from the group of synthetic, semisynthetic and natural oils, e.g. olive oil, sunflower oil, soya oil, peanut oil, rapeseed oil, almond oil, palm oil, coconut oil, palm kernel oil and the like.

Any mixtures of such oil and wax components can also be used advantageously for the purposes of the present invention. In some instances, it may also be advantageous to use waxes, for example cetyl palmitate, as the sole lipid component of the oil phase.

The oil phase is advantageously chosen from the group consisting of 2-ethylhexyl isostearate, octyidodecanol, isotridecyl isononanoate, isoeicosane, 2-ethylhexyl cocoate, $C_{12-15}$-alkyl benzoate, caprylic/capric triglyceride, dicaprylyl ether.

Particularly advantageous mixtures are those of $C_{12-15}$-alkyl benzoate and 2-ethylhexyl isostearate, those of $C_{12-15}$-alkyl benzoate and isotridecyl isononanoate, and those of $C_{12-15}$-alkyl benzoate, 2-ethylhexyl isostearate and isotridecyl isononanoate.

Of the hydrocarbons, paraffin oil, squalane and squalene are to be used advantageously for the purposes of the present invention.

Advantageously, the oil phase can also have a content of cyclic or linear silicone oils, or consist entirely of such oils, although it is preferred to use an additional content of other oil phase components apart from the silicone oil or the silicone oils.

Cyclomethicone (octamethylcyclotetrasiloxane) is advantageously used as the silicone oil to be used according to the invention. However, other silicone oils can also be used advantageously for the purposes of the present invention, for example hexamethylcyclo-trisiloxane, polydimethylsiloxane, poly(methylphenylsiloxane).

Mixtures of cyclomethicone and isotridecyl isononanoate, and of cyclomethicone and 2-ethylhexyl isostearate are also particularly advantageous.

The aqueous phase of the preparations according to the invention optionally advantageously comprises alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol, glycerol and, in particular, one or more thickeners which can advantageously be chosen from the group consisting of silicon dioxide, aluminium silicates, polysaccharides and derivatives thereof, e.g. hyaluronic acid, xanthan gum, hydroxypropylmethylcellulose, particularly advantageously from the group of polyacrylates, preferably a polyacrylate from the group of Carbopols, for example Carbopol grades 980, 981, 1382, 2984, 5984, in each case individually or in combination.

Preparations according to the invention which are in the form of emulsions comprise one or more emulsifiers. O/W emulsifiers can, for example, be advantageously chosen from the group of polyethoxylated or polypropoxylated or polyethoxylated and polypropoxylated products, e.g.:

of fatty alcohol ethoxylates,
of ethoxylated wool wax alcohols,
of polyethylene glycol ethers of the general formula R—O—(—CH$_2$—CH$_2$—O—)$_n$—R',
of fatty acid ethoxylates of the general formula R—COO—(—CH$_2$—CH$_2$—O—)$_n$—H,
of etherified fatty acid ethoxylates of the general formula R—COO—(—CH$_2$—CH$_2$—O—)$_n$—R',
of esterified fatty acid ethoxylates of the general formula R—COO—(—CH$_2$—CH$_2$—O—)$_n$—C(O)—R',
of polyethylene glycol glycerol fatty acid esters,
of ethoxylated sorbitan esters,
of cholesterol ethoxylates,
of ethoxylated triglycerides,
of alkyl ether carboxylic acids of the general formula R—O—(—CH$_2$—CH$_2$—O—)$_n$—CH$_2$—COOH where n is a number from 5 to 30,
of polyoxyethylene sorbitol fatty acid esters,
of alkyl ether sulphates of the general formula R—O—(—CH$_2$—CH$_2$—O—)$_n$—SO$_3$—H,
of fatty alcohol propoxylates of the general formula R—O—(—CH$_2$—CH(CH$_3$)—O—)$_n$—H,
of polypropylene glycol ethers of the general formula R—O—(—CH$_2$—CH(CH$_3$)—O—)$_n$—R', of propoxylated wool wax alcohols,
of etherified fatty acid propoxylates R—COO—(—CH$_2$—CH(CH$_3$)—O—)$_n$—R',
of esterified fatty acid propoxylates of the general formula R—COO—(—CH$_2$—CH(CH$_3$)—O—)$_n$—C(O)—R',
of fatty acid propoxylates of the general formula R—COO—(—CH$_2$—CH(CH$_3$)—O—)$_n$—H,
of polypropylene glycol glycerol fatty acid esters,
of propoxylated sorbitan esters,
of cholesterol propoxylates,
of propoxylated triglycerides,
of alkyl ether carboxylic acids of the general formula R—O—(—CH$_2$—CH(CH$_3$)O—)$_n$—CH$_2$—COOH,
of alkyl ether sulphates or the parent acids of these sulphates of the general formula R—O—(—CH$_2$—CH(CH$_3$)—O—)$_n$—SO$_3$—H,
of fatty alcohol ethoxylates/propoxylates of the general formula R—O—X$_n$—Y$_m$—H,
of polypropylene glycol ethers of the general formula R—O—X$_n$—Y$_m$—R',
of etherified fatty acid propoxylates of the general formula R—COO—X$_n$—Y$_m$—R',
of fatty acid ethoxylates/propoxylates of the general formula R—COO—X$_n$—Y$_m$—H.

According to the invention, the polyethoxylated or polypropoxylated or polyethoxylated and polypropoxylated O/W emulsifiers used are particularly advantageously chosen from the group of substances having HLB values of 11–18, very particularly advantageously having HLB values of 14.5–15.5, provided the O/W emulsifiers have saturated radicals R and R'. If the O/W emulsifiers have unsaturated radicals R and/or R', or isoalkyl derivatives are present, then the preferred HLB value of such emulsifiers can be lower or higher.

It is advantageous to choose the fatty alcohol ethoxylates from the group of ethoxylated stearyl alcohols, cetyl alcohols, cetylstearyl alcohols (stearyl alcohols). Particular preference is given to:

polyethylene glycol(13) stearyl ether (steareth-13), polyethylene glycol(14) stearyl ether (steareth-14), polyethylene glycol(15) stearyl ether (steareth-15), polyethylene glycol (16) stearyl ether (steareth-16), polyethylene glycol(17) stearyl ether (steareth-17), polyethylene glycol(18) stearyl ether (steareth-18), polyethylene glycol(19) stearyl ether (steareth-19), polyethylene glycol(20) stearyl ether (steareth-20),
polyethylene glycol (12) isostearyl ether (isosteareth-12), polyethylene glycol(13) isostearyl ether (isosteareth-13), polyethylene glycol(14) isostearyl ether (isosteareth-14), polyethylene glycol(15) isostearyl ether (isosteareth-15), polyethylene glycol(16) isostearyl ether (isosteareth-16), polyethylene glycol(17) isostearyl ether (isosteareth-17), polyethylene glycol(18) isostearyl ether (isosteareth-18), polyethylene glycol(19) isostearyl ether (isosteareth-19), polyethylene glycol(20) isostearyl ether (isosteareth-20),
polyethylene glycol(13) cetyl ether (ceteth-13), polyethylene glycol(14) cetyl ether (ceteth-14), polyethylene glycol (15) cetyl ether (ceteth-15), polyethylene glycol(16) cetyl ether (ceteth-16), polyethylene glycol(17) cetyl ether (ceteth-17), polyethylene glycol(18) cetyl ether (ceteth-18), polyethylene glycol(19) cetyl ether (ceteth-19), polyethylene glycol(20) cetyl ether (ceteth-20),
polyethylene glycol(13) isocetyl ether (isoceteth-13), polyethylene glycol(14) isocetyl ether (isoceteth-14), polyethylene glycol(15) isocetyl ether (isoceteth-15), polyethylene glycol(16) isocetylether (isoceteth-16), polyethylene glycol(17) isocetyl ether (isoceteth-17), polyethylene glycol(18) isocetyl ether (isoceteth-18), polyethylene glycol(19) isocetyl ether (isoceteth-19), polyethylene glycol(20) isocetyl ether (isoceteth-20),
polyethylene glycol(12) oleyl ether (oleth-12), polyethylene glycol(13) oleyl ether (oleth-13), polyethylene glycol(14) oleyl ether (oleth-14), polyethylene glycol(15) oleyl ether (oleth-15),
polyethylene glycol(12) lauryl ether (laureth-12), polyethylene glycol(12) isolauryl ether (isolaureth-12),
polyethylene glycol(13) cetylstearyl ether (ceteareth-13), polyethylene glycol(14) cetylstearyl ether (ceteareth-14), polyethylene glycol(15) cetylstearyl ether (ceteareth-15), polyethylene glycol(16) cetylstearyl ether (ceteareth-16), polyethylene glycol(17) cetylstearyl ether (ceteareth-17), polyethylene glycol(18) cetylstearyl ether (ceteareth-18), polyethylene glycol(19) cetylstearyl ether (ceteareth-19), polyethylene glycol(20) cetylstearyl ether (ceteareth-20).

It is also advantageous to choose the fatty acid ethoxylates from the following group:

polyethylene glycol(20) stearate, polyethylene glycol(21) stearate, polyethylene glycol(22) stearate, polyethylene glycol(23) stearate, polyethylene glycol(24) stearate, polyethylene glycol(25) stearate,
polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol(23) isostearate, polyethylene glycol(24) isostearate, polyethylene glycol(25) isostearate,
polyethylene glycol(12) oleate, polyethylene glycol(13) oleate, polyethylene glycol(14) oleate, polyethylene glycol(15) oleate, polyethylene glycol(16) oleate, polyethylene glycol(17) oleate, polyethylene glycol(18) oleate, polyethylene glycol(19) oleate, polyethylene glycol(20) oleate.

Sodium laureth-11 carboxylate can advantageously be used as the ethoxylated alkyl ether carboxylic acid or salt thereof.

Sodium laureth-14 sulphate can advantageously be used as alkyl ether sulphate.

Polyethylene glycol(30) cholesteryl ether can advantageously be used as ethoxylated cholesterol derivative. Polyethylene glycol(25) soyasterol has also proven successful.

The polyethylene glycol(60) evening primrose glycerides can advantageously be used as ethoxylated triglycerides.

It is also advantageous to choose the polyethylene glycol glycerol fatty acid esters from the group polyethylene glycol (20) glyceryl laurate, polyethylene glycol(21) glyceryl laurate, polyethylene glycol(22) glyceryl laurate, polyethylene glycol(23) glyceryl laurate, polyethylene glycol(6) glyceryl caprate/caprinate, polyethylene glycol(20) glyceryl oleate, polyethylene-glycol(20) glyceryl isostearate, polyethylene glycol(18) glyceryl oleate/cocoate.

It is likewise favourable to choose the sorbitan esters from the group polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate.

Advantageous W/O emulsifiers which can be used are: fatty alcohols having 8 to 30 carbon atoms, monoglycerol esters of saturated and/or unsaturated, branched and/or unbranched alkanecarboxylic acids having a chain length of from 8 to 24, in particular 12–18, carbon atoms, diglycerol esters of saturated and/or unsaturated, branched and/or unbranched alkanecarboxylic acids having a chain length of from 8 to 24, in particular 12–18, carbon atoms, monoglycerol ethers of saturated and/or unsaturated, branched and/or unbranched alcohols having a chain length of from 8 to 24, in particular 12–18, carbon atoms, diglycerol ethers of saturated and/or unsaturated, branched and/or unbranched alcohols having a chain length of from 8 to 24, in particular 12–18, carbon atoms, propylene glycol esters of saturated and/or unsaturated, branched and/or unbranched alkanecarboxylic acids having a chain length of from 8 to 24, in particular 12–18, carbon atoms, and sorbitan esters of saturated and/or unsaturated, branched and/or unbranched alkanecarboxylic acids having a chain length of from 8 to 24, in particular 12–18, carbon atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2) stearyl ether (steareth-2), glyceryl monolaurate, glyceryl monocaprinate, glyceryl monocaprylate.

Particularly suitable emulsifiers are glyceryl stearate citrate, glyceryl stearate, PEG esters of stearic acid, and the combination glyceryl stearate/stearic acid.

Gels used according to the invention usually comprise alcohols of low carbon number, e.g. ethanol, isopropanol, 1,2-propanediol, glycerol and water or an abovementioned oil in the presence of a thickener which, in the case of oily alcoholic gels, is preferably silicon dioxide or an aluminium silicate, and, in the case of aqueous-alcoholic or alcoholic gels, is preferably a polyacrylate.

Solid sticks comprise, for example, natural or synthetic waxes, fatty alcohols or fatty acid esters.

Customary bases which are suitable for use as cosmetic sticks for the purposes of the present invention are liquid oils (e.g. paraffin oils, castor oil, isopropyl myristate), semisolid constituents (e.g. vaseline, lanolin), solid constituents (e.g. beeswax, ceresine and microcrystalline waxes and ozokerite) and high-melting waxes (e.g. carnauba wax, candelilla wax).

Suitable propellants for cosmetic and/or dermatological preparations which can be sprayed from aerosol containers for the purposes of the present invention are the customary known readily volatile, liquefied propellants, for example hydrocarbons (propane, butane, isobutane), which can be used alone or in a mixture with one another. Compressed air can also be used advantageously.

The person skilled in the art is of course aware that there are propellants which are nontoxic per se and are in principle suitable for realizing the present invention in the form of aerosol preparations, but which must nevertheless be avoided because of their unacceptable impact on the environment or other accompanying circumstances, in particular fluorinated hydrocarbons and chlorofluorocarbons (CFCs).

For the purposes of the present invention, cosmetic preparations can also be in the form of gels which, in addition to an effective content of the active ingredient according to the invention and solvents customarily used therefor, preferably water, also comprise organic thickeners, e.g. gum arabic, xanthan gum, sodium alginate, cellulose derivatives, preferably methylcellulose, hydroxymethylcellulose, hydroxyethylcellulose, hydroxypropylcellulose, hydroxypropylmethylcellulose or inorganic thickeners, e.g. aluminium silicates, such as, for example, bentonites, or a mixture of polyethylene glycol and polyethylene glycol stearate or distearate. The thickener is present in the gel, for example, in an amount between 0.1 and 30% by weight, preferably between 0.5 and 15% by weight.

The examples below serve to illustrate the present invention without limiting it. Unless stated otherwise all amounts, proportions and percentages are based on the weight and the total amount or on the total weight of the preparations.

PREPARATION EXAMPLE 1

Half a molar equivalent, based on the amount of cyclodextrin, of Coenzyme Q10 is slowly added to a saturated aqueous α-cyclodextrin solution with vigorous stirring at room temperature. The mixture is further stirred overnight. The product (=molecular adduct 1) which precipitates out is filtered using a ceramic filter under reduced pressure, then washed with distilled water, dried and ground to give micronized particles.

PREPARATION EXAMPLE 2

Half a molar equivalent, based on the amount of cyclodextrin, of Coenzyme Q10 in the form of an aqueous suspension is slowly added to a saturated aqueous α-cyclodextrin solution with vigorous stirring at 50° C. The mixture is left to cool to room temperature and further stirred overnight. The product (=molecular adduct 2) which precipitates out is filtered using a ceramic filter under reduced pressure, then washed with distilled water, dried and ground to give micronized particles.

PREPARATION EXAMPLE 3

Half a molar equivalent, based on the amount of cyclodextrin, of Coenzyme Q10 is slowly added to a saturated aqueous β-cyclodextrin solution with vigorous stirring at room temperature. The mixture is further stirred overnight. The product (=molecular adduct 3) which precipitates out is filtered using a ceramic filter under reduced pressure, then washed with distilled water, dried and ground to give micronized particles.

PREPARATION EXAMPLE 4

Half a molar equivalent, based on the amount of cyclodextrin, of Coenzyme Q10 in the form of an aqueous suspension is slowly added to a saturated aqueous β-cyclodextrin solution with vigorous stirring at 70° C. The mixture is left to cool to room temperature and further stirred overnight. The product (=molecular adduct 4) which precipitates out is filtered using a ceramic filter under reduced pressure, then washed with distilled water, dried and ground to give micronized particles.

PREPARATION EXAMPLE 5

Half a molar equivalent, based on the amount of cyclodextrin, of Coenzyme Q10 is slowly added to a saturated aqueous γ-cyclodextrin solution with vigorous stirring at room temperature. The mixture is further stirred overnight. The product (=molecular adduct 5) which precipitates out is filtered using a ceramic filter under reduced pressure, then washed with distilled water, dried and ground to give micronized particles.

PREPARATION EXAMPLE 6

Half a molar equivalent, based on the amount of cyclodextrin, of Coenzyme Q10 in the form of an aqueous suspension is slowly added to a saturated aqueous γ-cyclodextrin solution with vigorous stirring at 80° C. The mixture is left to cool to room temperature and further stirred overnight. The product (=molecular adduct 6) which precipitates out is filtered using a ceramic filter under reduced pressure, then washed with distilled water, dried and ground to give micronized particles.

EXAMPLE 1

O/W Cream

| | % by weight |
|---|---|
| Glyceryl stearate citrate | 2.00 |
| Stearyl alcohol | 5.00 |
| Caprylic/capric triglycerides | 4.00 |
| Octyldodecanol | 4.00 |
| Glycerol | 3.00 |
| Carbomer | 0.10 |
| Molecular adduct 1 | 0.015 |
| (Coenzyme Q10, active in α-cyclodextrin complex) | |
| Sodium hydroxide | q.s. |
| Preservative | q.s. |
| Perfume | q.s. |
| Water, demineralized | ad 100.00 |
| pH adjusted to 6.0 | |

EXAMPLE 2

O/W Cream

| | % by weight |
|---|---|
| Glyceryl stearate citrate | 3.00 |
| Cetyl stearyl alcohol | 3.00 |
| Paraffin oil | 2.00 |
| Caprylic/capric triglycerides | 4.00 |
| Dicaprylyl ether | 3.00 |
| Xanthan gum | 0.10 |
| Citric acid | 0.10 |
| Sodium citrate | 0.20 |
| Molecular adduct 1 | 0.010 |
| (Coenzyme Q10, active in α-cyclodextrin complex) | |
| Glycerol | 3.00 |
| Preservative | q.s. |
| Perfume | q.s. |
| Water | ad 100.00 |
| pH adjusted to 5.5 | |

EXAMPLE 3

O/W Cream

| | % by weight |
|---|---|
| Glyceryl stearate SE | 4.00 |
| PEG-40 stearate | 1.00 |
| Cetyl alcohol | 3.00 |
| Caprylic/capric triglycerides | 5.00 |
| Paraffin oil | 5.00 |
| Glycerol | 3.00 |
| Carbomer | 0.10 |
| Molecular adduct 1 | 0.025 |
| (Coenzyme Q10, active in α-cyclodextrin complex) | |
| Sodium hydroxide | q.s. |
| Preservative | q.s. |
| Perfume | q.s. |
| Water, demineralized | ad 100.00 |
| pH adjusted to 5.0 | |

EXAMPLE 4

O/W Cream

| | % by weight |
|---|---|
| Glyceryl stearate SE | 3.00 |
| Stearic acid | 1.00 |
| Cetyl alcohol | 2.00 |
| Dicaprylyl ether | 4.00 |
| Caprylic/capric triglycerides | 3.00 |
| Paraffin oil | 2.00 |
| Glycerol | 3.00 |
| Butylene glycol | 3.00 |
| Carbomer | 0.10 |
| Molecular adduct 1 | 0.020 |
| (Coenzyme Q10, active in α-cyclodextrin complex) | |
| Sodium hydroxide | q.s. |
| Preservative | q.s. |
| Perfume | q.s. |
| Water, demineralized | ad 100.00 |
| pH adjusted to 7.0 | |

EXAMPLE 5

O/W Lotion

| | % by weight |
|---|---|
| Glyceryl stearate, Ceteth-20 | 1.00 |
| Sorbitan stearate | 1.00 |
| Stearyl alcohol | 1.00 |
| Caprylic/capric triglycerides | 2.00 |
| Paraffin oil | 4.00 |
| Glycerol | 3.00 |
| Carbomer | 0.10 |
| Molecular adduct 1 | 0.010 |
| (Coenzyme Q10, active in α-cyclodextrin complex) | |
| Sodium hydroxide | q.s. |
| Preservative | q.s. |
| Perfume | q.s. |
| Water, demineralized | ad 100.00 |
| pH adjusted to 5.5 | |

EXAMPLE 6

Emulsion Make-up

| | % by weight |
|---|---|
| Glyceryl stearate SE | 5.00 |
| Stearyl alcohol | 2.00 |
| Dimethicone | 2.00 |
| Glycerol | 3.00 |
| Carbomer | 0.15 |
| Mica | 1.00 |
| Magnesium silicate | 1.00 |
| Iron oxides | 1.00 |
| Titanium dioxide | 2.50 |
| Talc | 5.00 |
| Molecular adduct 1 | 0.015 |
| (Coenzyme Q10, active in α-cyclodextrin complex) | |
| Sodium hydroxide | q.s. |
| Preservative | q.s. |
| Perfume | q.s. |
| Water, demineralized | ad 100.00 |
| pH adjusted to 6.0 | |

EXAMPLE 7

W/O/W Cream

| | % by weight |
|---|---|
| Glyceryl stearate SE | 3.00 |
| PEG-100 stearate | 0.75 |
| Behenyl alcohol | 2.00 |
| Caprylic/capric triglycerides | 8.0 |
| Octyldodecanol | 5.00 |
| $C_{12-15}$-alkyl benzoates | 3.00 |
| Panthenol | 3.00 |
| $MgSO_4$ | 0.80 |
| Molecular adduct 1 | 0.020 |
| (Coenzyme Q10, active in α-cyclodextrin complex) | |
| Preservative | q.s. |
| Perfume | q.s. |
| Water, demineralized | ad 100.00 |
| pH adjusted to 6.0 | |

EXAMPLE 8

Hydrodispersion Gel

| | % by weight |
|---|---|
| Carbomer | 0.40 |
| Xanthan gum | 0.20 |
| Cetyl stearyl alcohol | 2.00 |
| $C_{12-15}$-alkyl benzoates | 5.00 |
| Caprylic/capric triglycerides | 3.00 |
| Glycerol | 3.00 |
| Molecular adduct 1 | 0.020 |
| (Coenzyme Q10, active in α-cyclodextrin complex) | |
| Sodium hydroxide | q.s. |
| Preservative | q.s. |
| Perfume | q.s. |
| Water, demineralized | ad 100.00 |
| pH adjusted to 5.5 | |

EXAMPLE 9

W/O Cream

| | % by weight |
|---|---|
| PEG-7 hydrogenated castor oil | 4.00 |
| Wool wax alcohol | 1.50 |
| Beeswax | 3.00 |
| Paraffin oil | 10.00 |
| Caprylic/capric triglycerides | 5.00 |
| Vaseline | 7.00 |
| Glycerol | 3.00 |
| $MgSO_4$ | 0.70 |
| Molecular adduct 2 | 0.010 |
| (Coenzyme Q10, active in α-cyclodextrin complex) | |
| Preservative | q.s. |
| Perfume | q.s. |
| Water, demineralized | ad 100.00 |

EXAMPLE 10

O/W Cream

| | % by weight |
|---|---|
| Glyceryl stearate citrate | 2.00 |
| Stearyl alcohol | 5.00 |
| Caprylic/capric triglycerides | 4.00 |
| Octyldodecanol | 4.00 |
| Glycerol | 3.00 |
| Carbomer | 0.10 |
| Molecular adduct 3 | 0.015 |
| (Coenzyme Q10, active in β-cyclodextrin complex) | |
| Sodium hydroxide | q.s. |
| Preservative | q.s. |
| Perfume | q.s. |
| Water, demineralized | ad 100.00 |
| pH adjusted to 6.0 | |

EXAMPLE 11

O/W Cream

| | % by weight |
|---|---|
| Glyceryl stearate citrate | 3.00 |
| Cetylstearyl alcohol | 3.00 |
| Paraffin oil | 2.00 |
| Caprylic/capric triglycerides | 4.00 |
| Dicaprylyl ether | 3.00 |
| Xanthan gum | 0.10 |
| Citric acid | 0.10 |
| Sodium citrate | 0.20 |
| Molecular adduct 3 | 0.010 |
| (Coenzyme Q10, active in β-cyclodextrin complex) | |
| Glycerol | 3.00 |
| Preservative | q.s. |
| Perfume | q.s. |
| Water | ad 100.00 |
| pH adjusted to 5.5 | |

EXAMPLE 12

O/W Cream

| | % by weight |
|---|---|
| Glyceryl stearate SE | 4.00 |
| PEG-40 stearate | 1.00 |
| Cetyl alcohol | 3.00 |
| Caprylic/capric triglycerides | 5.00 |
| Paraffin oil | 5.00 |
| Glycerol | 3.00 |
| Carbomer | 0.10 |
| Molecular adduct 3 | 0.025 |
| (Coenzyme Q10, active in β-cyclodextrin complex) | |
| Sodium hydroxide | q.s. |
| Preservative | q.s. |
| Perfume | q.s. |
| Water, demineralized | ad 100.00 |
| pH adjusted to 5.0 | |

EXAMPLE 13

O/W Cream

| | % by weight |
|---|---|
| Glyceryl stearate SE | 3.00 |
| Stearic acid | 1.00 |
| Cetyl alcohol | 2.00 |
| Dicaprylyl ether | 4.00 |
| Caprylic/capric triglycerides | 3.00 |
| Paraffin oil | 2.00 |
| Glycerol | 3.00 |
| Butylene glycol | 3.00 |
| Carbomer | 0.10 |
| Molecular adduct 3 | 0.020 |
| (Coenzyme Q10, active in β-cyclodextrin complex) | |
| Sodium hydroxide | q.s. |
| Preservative | q.s. |
| Perfume | q.s. |
| Water, demineralized | ad 100.00 |
| pH adjusted to 7.0 | |

EXAMPLE 14

O/W Lotion

| | % by weight |
|---|---|
| Glyceryl stearate, Ceteth-20 | 1.00 |
| Sorbitan stearate | 1.00 |
| Stearyl alcohol | 1.00 |
| Caprylic/capric triglycerides | 2.00 |
| Paraffin oil | 4.00 |
| Glycerol | 3.00 |
| Carbomer | 0.10 |
| Molecular adduct 3 | 0.010 |
| (Coenzyme Q10, active in β-cyclodextrin complex) | |
| Sodium hydroxide | q.s. |
| Preservative | q.s. |
| Perfume | q.s. |
| Water, demineralized | ad 100.00 |
| pH adjusted to 5.5 | |

EXAMPLE 15

Emulsion Make-Up

| | % by weight |
|---|---|
| Glyceryl stearate SE | 5.00 |
| Stearyl alcohol | 2.00 |
| Dimethicone | 2.00 |
| Glycerol | 3.00 |
| Carbomer | 0.15 |
| Mica | 1.00 |
| Magnesium silicate | 1.00 |
| Iron oxide | 1.00 |
| Titanium dioxide | 2.50 |
| Talc | 5.00 |
| Molecular adduct 3 | 0.015 |
| (Coenzyme Q10, active in β-cyclodextrin complex) | |
| Sodium hydroxide | q.s. |
| Preservative | q.s. |
| Perfume | q.s. |
| Water, demineralized | ad 100.00 |
| pH adjusted to 6.0 | |

EXAMPLE 16

W/O/W Cream

| | % by weight |
|---|---|
| Glyceryl stearate SE | 3.00 |
| PEG-100 stearate | 0.75 |
| Behenyl alcohol | 2.00 |
| Caprylic/capric triglycerides | 8.0 |
| Octyldodecanol | 5.00 |
| $C_{12-15}$-alkyl benzoates | 3.00 |
| Panthenol | 3.00 |
| $MgSO_4$ | 0.80 |
| Molecular adduct 3 | 0.020 |
| (Coenzyme Q10, active in β-cyclodextrin complex) | |
| Preservative | q.s. |
| Perfume | q.s. |
| Water, demineralized | ad 100.00 |
| pH adjusted to 6.0 | |

EXAMPLE 17

Hydrodispersion Gel

| | % by weight |
|---|---|
| Carbomer | 0.40 |
| Xanthan gum | 0.20 |
| Cetylstearyl alcohol | 2.00 |
| $C_{12-15}$-alkyl benzoate | 5.00 |
| Caprylic/capric triglycerides | 3.00 |
| Glycerol | 3.00 |
| Molecular adduct 1 | 0.020 |
| (Coenzyme Q10, active in β-cyclodextrin complex) | |
| Sodium hydroxide | q.s. |
| Preservative | q.s. |
| Perfume | q.s. |
| Water, demineralized | ad 100.00 |
| pH adjusted to 5.5 | |

EXAMPLE 18

W/O Cream

|  | % by weight |
|---|---|
| PEG-7 hydrogenated castor oil | 4.00 |
| Wool wax alcohol | 1.50 |
| Beeswax | 3.00 |
| Paraffin oil | 10.00 |
| Caprylic/capric triglycerides | 5.00 |
| Vaseline | 7.00 |
| Glycerol | 3.00 |
| $MgSO_4$ | 0.70 |
| Molecular adduct 4 | 0.010 |
| (Coenzyme Q10, active in β-cyclodextrin complex) | |
| Preservative | q.s. |
| Perfume | q.s. |
| Water, demineralized | ad 100.00 |

EXAMPLE 19

O/W Cream

|  | % by weight |
|---|---|
| Glyceryl stearate citrate | 2.00 |
| Stearyl alcohol | 5.00 |
| Caprylic/capric triglycerides | 4.00 |
| Octyldodecanol | 4.00 |
| Glycerol | 3.00 |
| Carbomer | 0.10 |
| Molecular adduct 5 | 0.015 |
| (Coenzyme Q10, active in γ-cyclodextrin complex) | |
| Sodium hydroxide | q.s. |
| Preservative | q.s. |
| Perfume | q.s. |
| Water, demineralized | ad 100.00 |
| pH adjusted to 6.0 | |

Example 20

O/W Cream

|  | % by weight |
|---|---|
| Glyceryl stearate citrate | 3.00 |
| Cetylstearyl alcohol | 3.00 |
| Paraffin oil | 2.00 |
| Caprylic/capric triglycerides | 4.00 |
| Dicaprylyl ether | 3.00 |
| Xanthan gum | 0.10 |
| Citric acid | 0.10 |
| Sodium citrate | 0.20 |
| Molecular adduct 5 | 0.010 |
| (Coenzyme Q10, active in γ-cyclodextrin complex) | |
| Glycerol | 3.00 |
| Preservative | q.s. |
| Perfume | q.s. |
| Water | ad 100.00 |
| pH adjusted to 5.5 | |

EXAMPLE 21

O/W Cream

|  | % by weight |
|---|---|
| Glyceryl stearate SE | 4.00 |
| PEG-40 stearate | 1.00 |
| Cetyl alcohol | 3.00 |
| Caprylic/capric triglycerides | 5.00 |
| Paraffin oil | 5.00 |
| Glycerol | 3.00 |
| Carbomer | 0.10 |
| Molecular adduct 5 | 0.025 |
| (Coenzyme Q10, active in γ-cyclodextrin complex) | |
| Sodium hydroxide | q.s. |
| Preservative | q.s. |
| Perfume | q.s. |
| Water, demineralized | ad 100.00 |
| pH adjusted to 5.0 | |

EXAMPLE 22

O/W Cream

|  | % by weight |
|---|---|
| Glyceryl stearate SE | 3.00 |
| Stearic acid | 1.00 |
| Cetyl alcohol | 2.00 |
| Dicaprylyl ether | 4.00 |
| Caprylic/capric triglycerides | 3.00 |
| Paraffin oil | 2.00 |
| Glycerol | 3.00 |
| Butylene glycol | 3.00 |
| Carbomer | 0.10 |
| Molecular adduct 5 | 0.020 |
| (Coenzyme Q10, active in γ-cyclodextrin complex) | |
| Sodium hydroxide | q.s. |
| Preservative | q.s. |
| Perfume | q.s. |
| Water, demineralized | ad 100.00 |
| pH adjusted to 7.0 | |

EXAMPLE 23

O/W Lotion

|  | % by weight |
|---|---|
| Glyceryl stearate, Ceteth-20 | 1.00 |
| Sorbitan stearate | 1.00 |
| Stearyl alcohol | 1.00 |
| Caprylic/capric triglycerides | 2.00 |
| Paraffin oil | 4.00 |
| Glycerol | 3.00 |
| Carbomer | 0.10 |
| Molecular adduct 5 | 0.010 |
| (Coenzyme Q10, active in γ-cyclodextrin complex) | |
| Sodium hydroxide | q.s. |
| Preservative | q.s. |
| Perfume | q.s. |
| Water, demineralized | ad 100.00 |
| pH adjusted to 5.5 | |

EXAMPLE 24

Emulsion Make-up

|  | % by weight |
|---|---|
| Glyceryl stearate SE | 5.00 |
| Stearyl alcohol | 2.00 |
| Dimethicone | 2.00 |
| Glycerol | 3.00 |
| Carbomer | 0.15 |
| Mica | 1.00 |
| Magnesium silicate | 1.00 |
| Iron oxide | 1.00 |
| Titanium dioxide | 2.50 |
| Talc | 5.00 |
| Molecular adduct 5 | 0.015 |
| (Coenzyme Q10, active in γ-cyclodextrin complex) | |
| Sodium hydroxide | q.s. |
| Preservative | q.s. |
| Perfume | q.s. |
| Water, demineralized | ad 100.00 |
| pH adjusted to 6.0 | |

EXAMPLE 25

W/O/W Cream

|  | % by weight |
|---|---|
| Glyceryl stearate SE | 3.00 |
| PEG-100 stearate | 0.75 |
| Behenyl alcohol | 2.00 |
| Caprylic/capric triglycerides | 8.0 |
| Octyldodecanol | 5.00 |
| $C_{12-15}$-alkyl benzoate | 3.00 |
| Panthenol | 3.00 |
| $MgSO_4$ | 0.80 |
| Molecular adduct 5 | 0.020 |
| (Coenzyme Q10, active in γ-cyclodextrin complex) | |
| Preservative | q.s. |
| Perfume | q.s. |
| Water, demineralized | ad 100.00 |
| pH adjusted to 6.0 | |

EXAMPLE 26

Hydrodispersion Gel

|  | % by weight |
|---|---|
| Carbomer | 0.40 |
| Xanthan gum | 0.20 |
| Cetylstearyl alcohol | 2.00 |
| $C_{12-15}$-alkyl benzoate | 5.00 |
| Caprylic/capric triglycerides | 3.00 |
| Glycerol | 3.00 |
| Molecular adduct 5 | 0.020 |
| (Coenzyme Q10, active in γ-cyclodextrin complex) | |
| Sodium hydroxide | q.s. |
| Preservative | q.s. |
| Perfume | q.s. |
| Water, demineralized | ad 100.00 |
| pH adjusted to 5.5 | |

EXAMPLE 27

W/O Cream

|  | % by weight |
|---|---|
| PEG-7 hydrogenated castor oil | 4.00 |
| Wool wax alcohol | 1.50 |
| Beeswax | 3.00 |
| Paraffin oil | 10.00 |
| Caprylic/capric triglycerides | 5.00 |
| Vaseline | 7.00 |
| Glycerol | 3.00 |
| $MgSO_4$ | 0.70 |
| Molecular adduct 6 | 0.010 |
| (Coenzyme Q10, active in γ-cyclodextrin complex) | |
| Preservative | q.s. |
| Perfume | q.s. |
| Water, demineralized | ad 100.00 |

What is claimed is:

1. A cosmetic or dermatological preparation comprising an active ingredient combination, said combination further comprising:
   (a) one or more cyclodextrins;
   (b) at least one quinone and/or at least one hydroquinone; and
   (c) wherein said combination of active ingredients is in a form suitable for topical administration, said form being selected from the group consisting of emulsions, microemulsions, oleogels, hydrodispersion and lipodispersions.

2. The cosmetic or dermatological preparation of claim 1, wherein the one or more cyolodextrins comprises one or more γ-cyclodextrins.

3. The cosmetic or dermatologloal preparation of claim 1, wherein at least one of the quinone derivatives is chosen from the group at ubiquinones.

4. The cosmetic or dermatologloal preparation of claim 1, wherein the quinone derivative is Coenzyme Q10.

5. The cosmetic or dermetological preparation of claim 1, wherein the active ingredient composition comprises molecular adducts formed between the cyclodextrins and the at least one quinone and/or at least one hydroquinone.

6. Active ingredients according to claim 5, wherein the active ingredient comprises at least one adduct having one of the following molar ratios:

1 mol of α-cyclodextrin:1 mol of quinone and/or hydroquinone;
   1 mol of β-cyclodextrin:1 mol of quinone and/or hydroquinone;
   1 mol of γ-cyclodextrin:1 mol of quinone and/or hydroquinone;
   2 mol of α-cyclodextrin:1 mol of quinone and/or hydroquinone;
   2 mol of β-cyclodextrin:1 mol of quinone and/or hydroquinone; 2 mol of γ-cyclodextrin:1 mol of quinone and/or hydroquinone;
   1 mol of α-cyclodextrin:2 mol of quinone and/or hydroquinone;
   1 mol of β-cyclodextrin:2 mol of quinone and/or hydroquinone;
   1 mol of γ-cyclodextrin:2 mol of quinone and/or hydroquinone;
   3 mol of α-cyclodextrin:1 mol of quinone and/or hydroquinone;

3 mol of β-cyclodextrin:1 mol of quinone and/or hydroquinone; and 3 mol of γ-cyclodextrin:1 mol of quinone and/or hydroquinone.

7. The cosmetic or dermatological preparation of claim 1, wherein the form suitable for topical administration is selected from the group consisting of, a cream, a lotion, an emulsion, gel, a spray, a powder, and a lipstick-like applicator.

8. The cosmetic dermatological preparation of claim 1, wherein the weight ratio of the cyclodextrins component to the quinone/hydroquinone component is between 0.2 to 10.

9. The cosmetic or dermatological preparation of claim 8, wherein the weight ratio of the cyclodextrin component to the quinone/hydroquinone component is between 0.5 to 8.

10. The cosmetic or dermatological preparation of claim 8, wherein the total amount of cyclodextrins is less than 20% of the total weight of the preparation.

11. The cosmetic or dermatological preparation of claim 10, wherein the total amount of cyclodextrins is less than 10% of the total weight of the preparation.

12. The cosmetic or dermatological preparation of claim 8, wherein the total weight of the quinone/hydroquinone component is less than 10% of the total weight of the preparation.

13. The cosmetic or dermatological preparation of claim 8, wherein the total amount of the quinone/hydroquinone component was less than 5% of the total weight of the preparation.

14. The cosmetic or dermatological preparation of claim 1, wherein the form for topical administration is not suitable for injection or ingestion by mouth.

15. The active ingredient combination of claim 1, wherein said combination further comprising molecular adducts formed between cyclodextrins and at least one quinone and/or at least one hydroquinone.

16. A method of treating and protecting skin, the method comprising applying to the skin an effective amount of the preparation of claim 1, further comprising molecular adducts formed between cyclodextrins and at least one quinone and/or at least one hydroquinone.

17. A cosmetic or dermatological preparation comprising an active ingredient combination, said combination further comprising (a) one or more cyclodextrins;

(b) at least one quinone and/or at least one hydroquinone; wherein (a) and (b) form a molecular adduct, and (c) wherein said combination of active ingredients is in a form suitable for topical administration, said form being selected from the group consisting of emulsions, microemulsions, oleogels, hydrodispersion and lipodispersions.

* * * * *